United States Patent [19]

Weber et al.

[11] 4,165,632

[45] Aug. 28, 1979

[54] METHOD OF MEASURING THE FLUIDITY OF LIQUIDS FOR MEDICAL AND PHARMACEUTICAL PURPOSES, AND APPARATUS FOR PERFORMING THE METHOD

[76] Inventors: Gerhard Weber, Wackenroderstr. 31, 8500 Nürnberg; Siegfried Peters, Lange Zeile 138, 8520 Erlangen; Jürgen Künzel, Am Pfarrbaum 1; Torsten Kreisel, Amalienstr. 43, both of 8500 Nürnberg, all of Fed. Rep. of Germany

[21] Appl. No.: 781,475

[22] Filed: Mar. 25, 1977

[30] Foreign Application Priority Data

Mar. 27, 1976 [DE] Fed. Rep. of Germany ....... 2613212
Dec. 24, 1976 [DE] Fed. Rep. of Germany ....... 2658799

[51] Int. Cl.² .................... G01N 11/08; G01N 33/16
[52] U.S. Cl. ........................................ 73/55; 128/1 R
[58] Field of Search ........................... 73/55; 128/2 G; 23/230 B

[56] References Cited

U.S. PATENT DOCUMENTS

| | | | |
|---|---|---|---|
| 3,115,768 | 12/1963 | Rhodes et al. | 73/55 |
| 3,720,097 | 3/1973 | Kron | 73/55 |
| 3,930,402 | 1/1976 | Detmar et al. | 73/55 |
| 3,990,295 | 11/1976 | Renovanz et al. | 73/55 |
| 3,999,538 | 12/1976 | Philpot, Jr. | 128/2 G |

FOREIGN PATENT DOCUMENTS 42-27439 12/1967 Japan ............................................. 73/55
210470 6/1968 U.S.S.R. ....................................... 73/55

OTHER PUBLICATIONS

Harkness, J., *A New Instrument for the Measurement of Plasma-Viscosity*. The Lancet, pp. 280–281, Aug. 1963.

*Primary Examiner*—Charles A. Ruehl
*Assistant Examiner*—Joseph W. Roskos
*Attorney, Agent, or Firm*—Holman & Stern

[57] ABSTRACT

A method and apparatus for determining the fluidity of a liquid such as blood or serum having the steps of drawing the liquid from the source through a capillary tube measuring cell into a reservoir unit and returning the liquid back through the tube at a constant flow velocity while measurements are made. The pressure difference between the ends of the capillary tube are directly related to the viscosity of the liquid.

27 Claims, 6 Drawing Figures

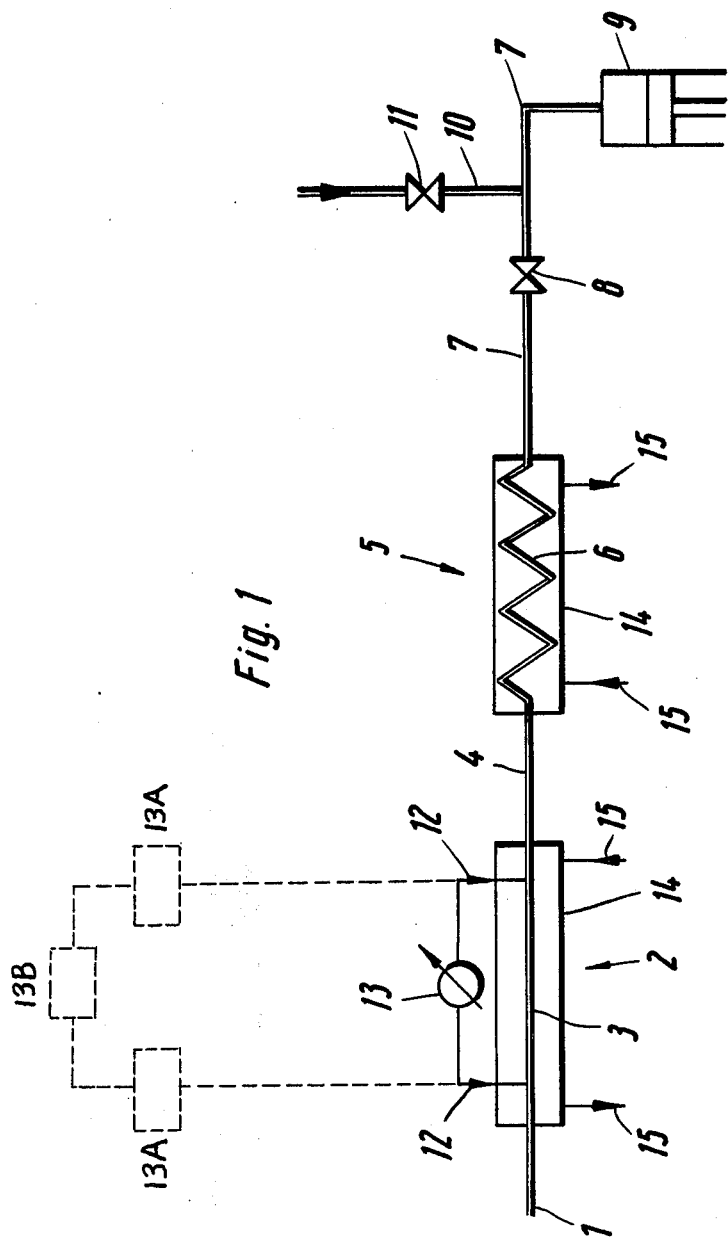

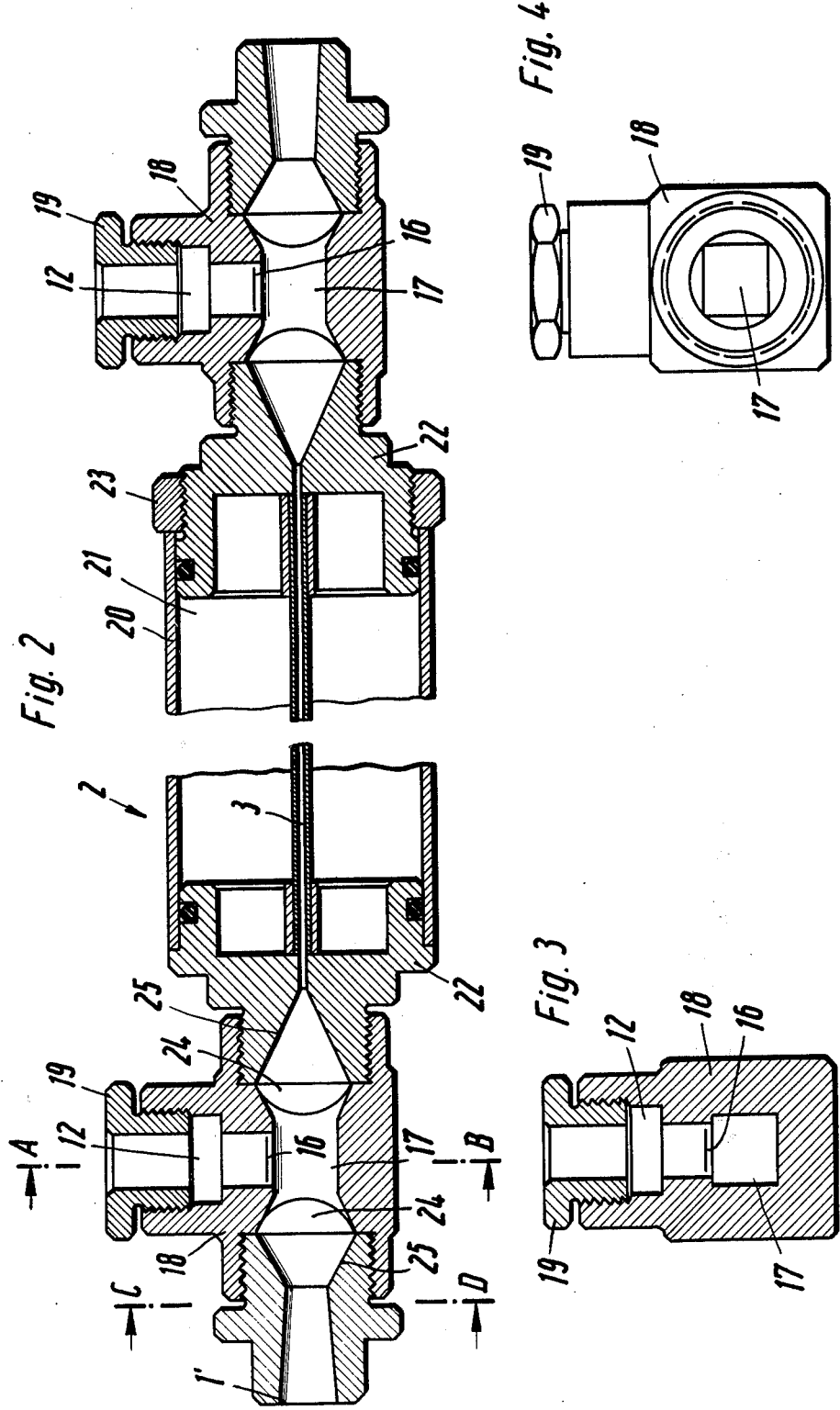

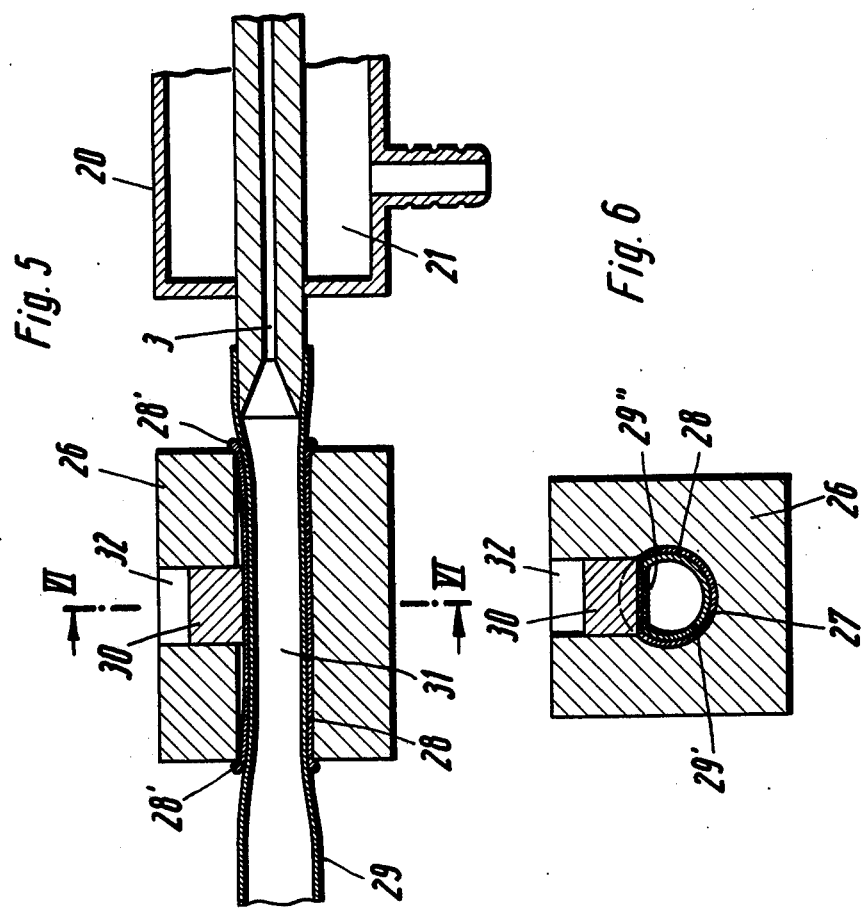

METHOD OF MEASURING THE FLUIDITY OF LIQUIDS FOR MEDICAL AND PHARMACEUTICAL PURPOSES, AND APPARATUS FOR PERFORMING THE METHOD

The invention primarily concerns a method of measuring the fluidity of liquids, in capillary tubes, for medical and pharmaceutical purposes. The contemplated liquids include for instance blood, infusion and transfusion solutions, and other liquids. The invention also relates to apparatus for performing the method.

Examination of the fluidity of blood and other physiologicalliquids, such as serum or lymph occupies a position of increasing importance and interest in modern medical practice. The principal desideratum is a rapid and precise measurement of the viscosity of the liquid. For instance, a change in the viscosity of the blood of a patient within a given period of time or in response to a treatment may be a significant factor in the diagnosis and therapy of a disease. For instance, in a suspected case of thrombosis, precise measurements of the coagulability of the blood would be desirable and an important indication would be that provided by the viscosity of the blood. During a particular course of treatment it is also often desirable to keep the viscosity of the blood of a patient under continuous observation, i.e., to carry out a large number of consecutive measurements at short intervals of time.

Similar or like problems arise in the pharmaceutical industry, for instance during the production of a serum, a transfusion liquid, and so forth in relatively small quantities, and it is nevertheless desired during the process of production to be aware of the viscosity of the liquid continuously.

In all the above mentioned cases the use of the methods conventionally employed of measuring viscosity in industrial processes, which comprise allowing a defined volume of liquid to flow through a capillary tube, measuring the viscosity by reference to time, and then discarding the tested volume of liquid, cannot be employed. This loss of liquid may not matter much when large volumes are being produced, but it cannot be accepted if the quantities that are available for such a measurement are only small and limited, such as blood taken from a patient or in the case of a serum when only a relatively small quantity is being prepared.

The measurements of viscosity which were hitherto carried out in such circumstances, for instance with the aid of rotary viscometers, such as the Couette, cone-plate viscometers, or the Hess viscometer, have diverse defects which are liable to introduce error. For example, when measuring the viscosity of blood a circumstance which is principally responsible for misleading results is that the time elapsing between the taking of a sample and the actual carrying out of the measurement is too long. When exposed to atmospheric oxygen or to the walls of its containing vessel the viscosity of a sample of blood already begins to change. Coagulation of the blood or rather its initial stages set in and vitiate the result. It is therefore the practice to stop or inhibit coagulation by the addition of heparin etc., before a viscometric measurement is actually performed. However, the fluidity of the blood is thereby considerably altered and in a manner that is not subject to control.

It is therefore an object of the present invention to provide a method, as well as an apparatus for performing the method, which for medical and pharmaceutical purposes will enable the fluidity of a liquid to be quickly and easily determined without any part of the liquid being lost and being discarded. Another object of the invention is to prevent the sample liquid from coming into contact with the ambient air or with parts of a component, such as a pump likely to affect the properties of the liquid. Yet another object is to provide apparatus that can be easily and quickly cleaned without having to be dismantled or taken apart.

For achieving the contemplated objects the invention firstly provides a method which comprises the steps of drawing the liquid on which the measurement is to be performed from its containing vessel, such as the human body or some other vessel, through a measuring cell containing a capillary tube into a reservoir unit and then expelling the liquid again into its original vessel through the measuring cell at a velocity of flow that remains constant for a certain period of time. This method has several advantages which are of special importance in the context of its application in medicine and pharmaceutics. The entire liquid that is to be measured is returned into the containing vessel from which it has been withdrawn, so that there is no loss. Once a connection to the containing vessel has been made many measurements can be carried out in rapid succession for long periods of time. This is particularly important when the changing fluidity of a liquid is to be kept under observation; as for instance, the viscosity of the blood of a human patient to assess the effects of a particular treatment, such as infusions, transfusions, the administration of particular drugs or during an operation and so forth. In pharmaceutical production, for instance, the viscosity of a liquid that is being prepared can be continuously monitored so that in the event of any deviation from a desired viscosity level steps can be taken to vary a parameter in the manufacturing process and the deviation corrected. If desired this may be done automatically by the provision of a controller which is fed with the results of the measurements. In other words, the overall result is a method of continuous measurement and possibly also of continuous control adapted to work without significant loss of liquid that is to be measured and/or controlled.

Moreover, the above described risk of the properties of such a liquid changing during an unavoidable period of delay before the measurement can be made and/or as a result of contact between the liquid and air is entirely eliminated. This is a matter of primary importance in viscosity measurements performed on human blood. On the one hand, the present method by its rapidity eliminates the risk to the patient involved in coagulation of the blood and, on the other hand, the true fluidity of the blood can be ascertained, faulty results caused by incipient coagulation and/or by the introduction of anticoagulants being avoided. The measurement is performed on the living unaltered blood which can be returned to the blood stream whence it was taken. These measurements which can be analogously performed on blood substitutes, plasma expanders, etc., are of great importance in medicine for the purpose of diagnosis, therapy and research. This importance is enhanced by the advantage that has already been mentioned, namely that the measurements can be very quickly and hence consecutively performed so that a continuous fluidity curve can be plotted in a very short time.

In a preferred mode of carrying the proposed method into effect the measured liquid is drawn into and re-expelled from the measuring system by pump means acting through an interposed buffer liquid, such as an infusion solution. This means that the liquid which is to be measured, e.g. blood, cannot come into contact with moving mechanical parts of the apparatus which might conceivably chemically react, with the liquid or give rise to the formation of air bubbles. If during the return of the blood a minor volume of this buffer solution, which must be a compatible solution, such as an infusion solution, should happen accidentally to enter the patient's blood stream, then no harm will be done. An infusion solution has no adverse effects on the blood. Another advantage of this particular step is that the buffer liquid, e.g. the infusion solution, can be used when the measurements have been completed to flush out and clean the measuring capillary and the tube in the reservoir unit, as well as the connecting pipe lines.

The invention also relates to apparatus for performing the proposed method comprising passing the liquid through a measuring capillary tube. In apparatus according to the invention one end of a measuring capillary tube is provided with means for connecting the same to the vessel containing the liquid that is to be measured, whereas the other end is connected to a reservoir unit, the measuring capillary tube being equipped with means for measuring the fluidity of the liquid that passes therethrough, and the reservoir unit being connected by a pipe line to means for drawing in and re-expelling the liquid that is to be measured, such as a plunger pump. Apparatus of this kind will permit the proposed method to be performed. The apparatus is easy to handle and the measurements can be quickly made. The construction of the apparatus is relatively straightforward and thus not liable to develop faults and the cost of production is correspondingly low. When the liquid is forced back through the capillary tube the presence of the reservoir unit functions to generate preliminary shear and therefore reduces the length of the entry zone in the capillary. The results of the measurements may either be visually read or recorded, or converted into electrical signals and introduced into a computer which may be provided with facilities for print-out of the results.

Other aspects and advantageous features of the method according to the invention and of the apparatus the invention proposed to use, as defined in appendant claims, will now be described in greater detail, purely by way of example and reference made to embodiments of the apparatus which are shown in the accompanying drawing in which FIG. 1 is a diagrammatic representation of apparatus according to the invention, FIG. 2 is a longitudinal section of one form of construction of the measuring cell containing the measuring capillary tube, FIG. 3 is a section taken on the line A-B in FIG. 2 and FIG. 4 is a section taken on the line C-D, omitting the part marked 1' in FIG. 2.

FIG. 5 is a further embodiment of the pressure-measuring device with the capillary tube shown in longitudinal cross-section;

FIG. 6 is a section taken on the line VI—VI in FIG. 5.

Referring to the drawings, the liquid upon which a measurement is to be performed, e.g. the blood of a patient is drawn through a pipe 1 into a measuring cell 2 containing a capillary tube 3. The measuring cell 2 is connected by a further length of pipe 4 to a reservoir unit 5 containing a reservoir tube 6 resembling a capillary tube. The other end of the reservoir unit is connected by yet another length of pipe 7 containing a stop valve 8 to a piston pump 9. Between the stop valve 8 and the piston pump 9 this pipe 7 communicates with a branch pipe 10 for the admission of an auxiliary buffer liquid adjusted so that it is compatible with the liquid that is to be measured. This branch 10 can be closed by another valve 11. If the measured liquid is blood, it is advisable that all parts, pipe-lines or connections of the apparatus with which the blood makes contact should be made of polyamide or, to the extent they preferably consist of a metal that this should be platinum or a high quality chrome-nickel stainless steel. Experiments have shown that compared with other materials the proposed materials substantially retard the coagulation of the blood that flows through such parts. More particularly, the connections 1 and 4 of the measuring capillary tube 3 to the vessel supplying the blood and to the reservoir unit 5 as well as the pipe connection 7 from the reservoir unit to the means for drawing the blood through the apparatus by suction and then forcing it back again, may consist of lengths of flexible polyamide tubing, whereas the measuring capillary tube 3 and the tube 6 in the reservoir unit 5 may preferably consist of platinum or stainless steel. This is preferred because the diameter of the capillary should be very precise. Such close manufacturing tolerances are easy to observe if this component is made of platinum or stainless steel. The employment of platinum or stainless steel for the tube 6 in the reservoir unit is advisable for manufacturing reasons. On the other hand, the less costly polyamide is quite satisfactory for the connections or pipes 1, 4 and 7. A polyamide pipe can be relatively long and its flexibility makes it more suitable for attaching it to the human body and for making the required connections than a rigid pipe.

Before the measurement begins the entire apparatus is filled with the buffer liquid, such as an infusion solution. The pipe 1 which does not affect the blood and which, more particularly, does not cause it to coagulate, is connected to the containing vessel, for instance by means of a catheter to the vein or right hand ventricle of the heart of a patient, and the blood or liquid is drawn into the apparatus, for instance in the apparatus in FIG. 1 by the displacement of the plunger in pump 9 downwards. The blood therefore flows through the measuring capillary tube 3, the pipe 4 and the tube 6, the infusion solution being displaced. The reservoir unit 5, i.e. the tube 6 which it contains, is filled with the measured liquid, e.g. the blood, only as far as will ensure that no blood enters the pipe connection 7 from the reservoir unit 5 to the pump 9. This will definitely prevent the liquid that is to be measured from coming into contact with the pumping system or with the valves 8 and 11.

In the apparatus illustrated in FIG. 1 the pump plunger 9 is then pushed upwards again, causing the buffer liquid to transmit a corresponding thrust to the liquid that is to be measured, which therefore now flows back through the measuring capillary tube 3, being displaced from the reservoir unit.

If the pump 9 should not generate a constant pressure the interposition of the reservoir unit ensures that the velocity of flow of the liquid that is to be measured through the measuring capillary tube 3 will in fact be constant, at least for a certain period of time sufficient for the measurement to be completed. The measuring elements in this apparatus may be precision pressure gauges 12 at each end of the capillary tube 3. A reading instrument 13 may be provided to indicate the difference between the two pressures or in a preferred embodiment of the invention, the measured quantities by appropriate means 13A may first be converted into electrical quantities. These electrical quantities in the form of currents or voltages derive from the pressure gauges, and possibly the current controlling the pump are fed to a computer 13B, which is arranged to print out the measured results, in the desired units or dimensions, for instance in a viscosity measurement in poises, as well as to convert the results of the measurements into a continuous fluidity curve. It may here be observed that the method according to the invention is particularly suitable for the performance of measurements on low viscosity liquids.

Operations of the pressure pump 9, e.g. the reciprocation of the plunger, may be automatic and proceed by reference to prescribed data, for instance by control of a motor operating the pump. It is thus possible to carry out measurement series in which the return flow of the liquid proceeds at specific though consecutively changing velocities. The velocity of flow of the measured liquid through the measuring capillary tube 3 is a function of the cross section of flow and the volume of liquid displaced per unit of time by the pump 9. Hence, after the apparatus has been filled the sample volume present in the measuring cell 2 and in the reservoir unit 5 can be forced through the capillary 3 by pushig the plunger of the pump 9 upwards at velocities which can be kept constant for a period of about 2 to 4 seconds. The pressure differential between the ends of the capillary tube which results when the pump displaces a given volume per unit of time is measured by the above described precision pressure gauges 12. A series of measurements for the determination of ten points of a fluidity curve will therefore take only about one minute to complete. If for rheological reasons (establishment or equilibrium of flow) a flow of longer duration at a given velocity of flow is desirable, then the entire sample volume of liquid contained in the reservoir unit can be forced through the capillary tube 3 at unchanging velocity. The above-mentioned computer can then provide a number of data, such as velocity of flow, shear stress, as well as viscosity. Moreover, these data can be fed to the data storage of a therapeutic or pharmaceutical programming unit which may control infusions and treatments during the treatment of a patient, and in pharmaceutical production, steps such as additions to the measured liquid and changes in processing parameters, such as temperature and so forth.

The mixing zone in which the liquid that is to be measured, for instance blood, mixes with the buffer liquid, such as an infusion solution, should be relatively short, e.g. 10 cms in length compared with a length of about 2 to 4 meters of the reservoir tube 6. In the illustrated example the diameter of the tube 6 will be about 2 mm, whereas the diameter of the measuring capillary tube 3 is about 1 mm, its length in this example being about 30 cms. However, it will be readily understood that the invention is not intended to be limited to these particular diameters and lengths which are here given purely by way of example. The diameter of the capillary should be a multiple, for instance ten times the diameter of the largest object contained in the liquid, such as the body of a cell. Moreover, the capillary should also be long enough to reduce the entry and exit effects on the viscosity measurement to negligible proportions. Furthermore, the above data may be varied according to the nature of the measured liquid. In accordance with the above explanations the so-called mixing zone will be located near the end of the reservoir tube where this joins the connecting pipe 7. It should be enough to surround the measuring cell 2 and the reservoir unit 5 with a conditioning or tempering jacket 14 through which a thermostatically controlled fluid can be circulated by pipe means 15. On the other hand, the pipes 7 and the pump 9 need not be temperature controlled. When the measurement or series of measurements has been completed, valve 8 is closed and valve 11 opened to permit an appropriate volume of buffer liquid to be drawn in through the branch pipe 10 by the pump 9. Valve 11 can then be reclosed and valve 8 reopened and the measuring sytem flushed out with the buffer liquid, such as an infusion solution. The entire apparatus should be continuously filled with buffer liquid except for the volume occupied by the measured liquid whilst this is being drawn in and forced out through the measuring unit 3 into and from the reservoir unit 5, as has been described.

As above-stated, the method according to the invention can also be used in pharmaceutical practice, for instance during the production of pharmaceutical preparations. For example, it may be important to know the viscosity of solutions of polymers. The preparation of sera has already been mentioned which, like blood, must also be prevented from coming into contact with air. Frequently, pharmaceutical products are prepared in small quantities and in such cases it will certainly be desirable that none of the measured liquid is lost. For example, it has been found that when performing the proposed method in apparatus according to the invention, the plotting of a continuous fluidity curve obtained from measurements at 10 different velocities of flow required only 12 mils of liquid and this would still be of use for carrying out other medical tests.

A possible form of construction of the measuring cell 2 is illustratively shown in FIGS. 2 to 4. 1' is the taper socket for the reception of the end of the entry pipe 1. The pressure gauge 12 contains a diaphragm 16 which is exposed to the pressure head of the liquid as it passes through a passage 17. In this arrangement, the diaphragm is provided with strain gauges which generate electrical signals that correspond to the existing pressure, and transmit them to the computer. Naturally, pressure gauges of some alternative type and construction could also be fitted, provided they were capable of performing the functions required for the purposes of the invention. The pressure gauge 12 is here shown fitted into a pipe union 18 incorporated in the pipe line for conveying the liquid.

Part 19 serves for securing the pressure gauge 12 in the pipe union 18. The pressure gauges 12 are so disposed at each end of the measuring capillary tube that the creation of sharp edges and angles of less than 90° is avoided to ensure that flow is not significantly affected or impaired in these zones. The cross section of the pipe union 18 which is fitted with the pressure gauge and particularly the cross section of the passage 17 is square (c.f. FIGS. 3 and 4) to permit the pressure gauge 12 to be a flush fit in the pipe union and the diaphragm 16 to be a flush fit with the inside surface of the passage 17. Moreover, the entry and exit openings 24 of the pipe union are conically flared, diverging like Laval nozzles and merging into the convergent tapers 25. This shape is flow dynamically favorable besides permitting these parts to be reliably and quickly cleaned. The diameter of the passage 17 is several times greater than the cross section of the capillary tube 3 so that no pressure loss that would adversely affect the measurement can occur outside the capillary.

The measuring cell 2 proper containing the measuring capillary tube 3 is surrounded by a jacket 20 and a liquid for the maintenance of a constant temperature can be circulated through the interior 21 of the jacket. 22 are holders for the measuring capillary tube 3 and the parts are held together by a milled ring nut 23. The right hand end of the capillary tube in FIG. 2 communicates with a similar pipe union 18 to that on the left containing a pressure gauge 12, diaphragm 16, and retaining screw ring 19.

FIGS. 5 and 6 show a further embodiment of the structure of the pressure-measuring arrangement. Also herein, as in the above embodiment of FIGS. 2 to 4, precision pressure-gauges are provided at both ends of the measuring capillaries, whereby a reading or registration of the pressure-difference is made. These precision pressure recordings may each show a practically pathless pressure-measuring device in which the changes of pressure (or thrust) in the liquid to be measured does not result in a substantial deformation or movement of a membrane or the like. Such a pathless pressure (or thrust) measuring device may, for example, be membranes which are provided with stretch-measuring tapes.

In contrast to the embodiments of FIGS. 2 to 4, in the arrangement according to FIGS. 5 and 6, the pressure (or thrust) measuring devices are located at the edge of the flow-cross-section of the liquid-inflow and liquid-outflow to the capillary tube 3 and are stressed by the pressure of the liquid. Only one of the two ends of the capillary is shown in the drawing. The portions of the pressure-measuring device described hereinbelow are duplicated in the other end of the measuring capillary, not shown in the drawing.

The capillary 3 is also restricted within the jacket 20 which is connected with the two casings 26. The space filled by the tempering liquid is denominated with 21.

In a substantially cylindrical borehole 27 of the casing 26, a measuring channel 28 is provided consisting of an elastic tube and being retained in the borehole 27, e.g., being glued therein. The ends 28' of the measuring channel may protrude at the front portions of the casing 26. A tube is insertable into the measuring channel 28, which tube also consists of an elastic material. The tubes, or respective tube-portions, may, for example, consist of a polyamide or a polyurethane plastic. The measuring channel 28 may consist of a corresponding material. The elasticity of the measuring channels 28 and the tube 29 is, at least in the area of the pressure-measuring organ 30, such that the inside pressure prevailing inside the tube of the liquid to be measured, is being transmitted through the tube-walls and the walls of the measuring channels to the measuring organs. Thus, the utilization of a tube, assymetrically located in its cross-section, is possible. The tube is shown in FIG. 6 at numeral 29' with its thicker circumference being of a stronger wall, and at numeral 29" with approximately ¼ portion of its circumference representing that portion which is of a thinner wall and accordingly, more elastic. The thicker circumference portion 29' guarantees a sufficient strength preventing the tube, during the sucking-in of the measuring liquid, from collapsing. The circumference portion 29" has such thin walls that it is able to transmit the pressure of the liquid. In the mounting position (see FIG. 2), the tube portion 29" is somewhat flattened and rests with initial stress on the measuring channel. Insofar as the measuring device 30 of this embodiment rests on the measuring channel, the latter is also flattened in the bearing area, whereby a sufficient pressure-transmitting area is produced. The outer diameter of the respective measuring tube 29 is preferably slightly larger than the inside diameter of the component measuring channel 28. Thus, the pressure in the measuring path 31 is transmitted by the tube to the wall of the measuring channel without the possibility that the elastic forces in the tube will influence the measuring.

The tubes 29 are insertable into the ends of the capillaries by penetrating the measuring channels.

They may, at the same time, serve as connecting means of the capillaries to the reservoir-unit or the vessel. The tubes may be one-way articles which are discarded after the measuring is completed; thus, eliminating the need for sterilization of these tubes after their use. For new measurements, they are replaced with new, sterile tubes. The measuring capillaries may then be sterilized in the common manner. In general, the portions containing the liquid can be constructed as explained in the embodiment of FIGS. 2 and 4.

There are proposed practically path-less pressure-recorders 30, for example in the form of stretch-measuring tapes, or half-conductor elements with a piezo-electric effect, or a different path-less pressure-measuring device. The utilization of path-less measuring devices has the advantage that practically no stretching of the measuring channel results and, in interference of the measuring by means of elasticity of the material of the measuring-channel wall is eliminated.

The embodiment of FIGS. 5 and 6 shows schematically a pressure-measuring device 30, which is provided with a membrane at the bottom-side resting on the measuring channel, said membrane being provided with stretch-measuring tapes. The membrane being located in a cavity 32 having a longitudinal axis which is vertical to the longitudinal axis of the borehole 27. The measuring members of the pressure recorder, for example stretch-measuring tapes, are located immediately on the outer walls of the measuring channel. It is also possible, instead, to place or glue stretch-measuring tapes or the like immediately onto the outer wall of the measuring channel. In such a case, the necessity for supplying the measuring channel with a level area would be eliminated, however, on the outer backside of the stretch-measuring tapes there would be a free space through which are guided the connecting tubes. It is guaranteed that the measuring channel does not come in contact with the medium to be measured, and, in addition, that the pressure-recorder is located at the outer side of the measuring channel, so that it cannot come into contact with the measuring liquid. The measuring channels prevent the liquid which is diffused through the tube during a length of time from coming into contact with the measuring members.

FIGS. 5 and 6 embodiments, in contrast to the embodiment of FIGS. 2 and 4, provide that the space which is to be filled by the liquid is limited to flow cross-section of the capillaries, the storage path and the inflow and outflow tubes. Dead-spaces in the area of the measuring arrangement are avoided. This produces several advantages. The test volume required for a measurement is accordingly reduced. This is of a special advantage in the determining of the flow-process of blood since one is thus able to perform measurements with a very small amount of blood taken, also repeatedly, from the patient, and in this case a pressing back of the blood into the vein is no longer required. Through the dead-spaces and the edges and corners, which are thereby present, the coagulation of blood can be improved. Also this is prevented with the arrangement of FIGS. 5 and 6. Furthermore, the elimination of dead spaces eases the cleaning and sterilization of the respective parts of the apparatus.

What is claimed is:

1. A method of determining the fluidity of a liquid, such as of blood or serum, in a capillary, for medical and pharmaceutical purposes, comprising the steps of drawing the liquid from a vessel, through a measuring cell containing a capillary tube into a reservoir unit and thereafter returning the liquid to its original vessel through the measuring cell while performing viscosity measurements at a velocity of flow that remains constant for a given period of time, said measured liquid being drawn into and expelled from the measuring cell by pump means through an interposed buffer liquid, such as an infusion solution.

2. The method according to claim 1, in which the liquid to be measured is drawn no further than will ensure that the pump means are wetted only by the buffer liquid and in which the entire volume of the apparatus not filled with the liquid to be measured is filled with the buffer liquid.

3. The method according to claim 2, in which at the end of a measurement fresh buffer liquid is drawn in through a branch supply pipe and that the measuring cell and the reservoir unit are flushed out with this buffer liquid.

4. The method according to claim 1, in which the pressure difference between the two ends of the measuring capillary tube is determined during the return of the liquid to its original vessel.

5. The method according to claim 4, in which the result of the measurement of the pressure difference is converted into electrical signals which are fed to a computer.

6. The method according to claim 5, in which a programmed control is provided to time the operation of the means for drawing in and returning the liquid to be measured.

7. The method according to claim 1, in which the measuring cell and the reservoir unit are maintained at a constant temperature.

8. An apparatus for determining the fluidity of a liquid, such as blood or serum, in a capillary, for medical and pharmaceutical purposes comprising:
a measuring capillary tube having two ends, a diameter, a length and a cross sectional area;
a source of the liquid; first connecting means for interconnecting said source to one end of said capillary tube;
a reservoir unit having two ends; second connecting means connecting one end of said reservoir unit to the other end of said capillary tube;
means for drawing in and returning said liquid through said capillary tube operatively associated with the other end of said reservoir unit;
third connecting means connecting said means for drawing and returning liquid to the other end of said reservoir unit; and
measuring means for measuring the fluidity of the liquid being passed through said capillary tube, said measuring means being operatively connected to said capillary tube.

9. The apparatus according to claim 8, wherein said reservoir comprises a tube having a diameter and a length, said diameter of said reservoir tube being of the same order of magnitude as the diameter of the capillary tube, both of said diameters being greater than the largest diameter of any object suspended in the liquid, and said length of said reservoir tube being longer than said length of said capillary tube.

10. The apparatus according to claim 9, wherein said first, second, and third connecting means are made from a material selected from the group consisting of polyamide plastic, platinum, and stainless steel.

11. The apparatus according to claim 10, wherein said first, second, and third connecting means are flexible tubing made of polyamide plastic and said capillary tube and said reservoir tube are made of a material selected from the group consisting of platinum and stainless steel.

12. The apparatus according to claim 8, further comprising
a first thermostatically controlled jacket surrounding in a temperature controlling relationship said capillary tube and
a second thermostatically controlled jacket surrounding in a temperature controlling relationship said reservoir unit.

13. The apparatus according to claim 8, wherein said measuring means comprises two precision pressure measuring devices, each connected to one end of said capillary tube and means for determining the difference in measurement of the devices.

14. The apparatus according to claim 13, wherein said measuring means further comprises means for converting the measurements of each of the devices to electrical signals and said means for determining the difference comprises a computer.

15. The apparatus according to claim 13, further comprising a first pipe union joining said first connecting means and one end of said capillary tube having a cross-sectional area, said pressure measuring device being fitted to said pipe union.

16. The apparatus according to claim 15, wherein said cross-sectional area of said pipe union is greater than said cross-sectional area of said capillary tube.

17. The apparatus according to claim 15, wherein said pressure measuring devices each comprise a diaphragm mounted in said pipe union and a strain gauge operatively connected to said diaphragm.

18. The apparatus according to claim 8, further comprising
additional fluid means for adding a buffer liquid connected to said third connecting means between said reservoir unit and said means for drawing in and returning said liquid through said capillary tube.

19. The apparatus according to claim 18, wherein said additional fluid means includes a first valve and said third connecting means includes a second valve between where said additional fluid means is connected and said reservoir unit.

20. The apparatus according to claim 8, wherein said measuring means are located at the edge of the flow cross-section of the ends of said capillary tube and are stressed by the pressure of the liquid.

21. The apparatus according to claim 20, said measuring means comprises two measuring channels, one being at each end of said capillary tube, and two measuring tubes, one at each end of said capillary tube mounted into the capillary tube and corresponding in size with the flow-cross-section of the liquid, said tubes being located within the measuring channels, the tubes and the measuring channels each consisting of an elastic, liquid-pressure-transmitting material, and a pressure-measuring device abutting the outer wall of the measuring channel.

22. The apparatus according to claim 21, wherein the outer diameter of each measuring tube is larger than the inner diameter of the respective measuring channel.

23. The apparatus according to claim 21, wherein the measuring channel comprises a piece of a tube which penetrates a borehole of a casing and is fastened therein, whereby the casing is provided with a cavity running vertical to the borehole, in which the pressure-measuring device is fastened.

24. The apparatus according to claim 21, wherein said pressure-measuring device comprises stretch-measuring tapes which are fastened immediately to the outside wall of the measuring channel.

25. The apparatus according to claim 21, wherein the tubes, at least in the area in which they affect the pressure-measuring device, within the measuring channel, are more elastic, being of a thinner wall, than in their remaining area.

26. The apparatus according to claim 21, wherein the tubes are arranged to be replaceable by being guidable through the measuring channels and insertable onto the ends of the capillary tube.

27. A method of determining the fluidity of a liquid, such as a blood or serum, in a capillary, for medical and pharmaceutical purposes, comprising the steps of drawing the liquid from a vessel, through a measuring cell containing a capillary tube onto a reservoir unit and thereafter returning the liquid to its original vessel through the meauring cell while performing viscosity measurements by determining the pressure difference between the two ends of the measuring capillary tube and converting the result of the measurement into electrical signals which are fed to a computer, said measurements being taken at a velocity of flow that remains constant for a given period of time, the liquid to be measured being forced through the measuring capillary tube at consecutively different velocities which are each kept constant for predetermined periods of time by a means for drawing in and returning the liquid, said means having a programmed control for timing the operation of the same.

* * * * *